United States Patent
Brown et al.

(10) Patent No.: US 7,064,137 B2
(45) Date of Patent: *Jun. 20, 2006

(54) 4-(PHENYL-(PIPERIDIN-4-YL)-AMINO)-BENZAMIDE DERIVATIES AND THEIR USE FOR THE TREATMENT OF PAIN, ANXIETY OR GASTROINTESTINAL DISORDERS

(75) Inventors: William Brown, Montreal (CA); Andrew Griffin, Montreal (CA); Christopher Walpole, Montreal (CA)

(73) Assignee: Astrazeneca AB, Sodertalje (SE)

( * ) Notice: Subject to any disclaimer, the term of this patent is extended or adjusted under 35 U.S.C. 154(b) by 30 days.

This patent is subject to a terminal disclaimer.

(21) Appl. No.: 10/477,853

(22) PCT Filed: May 16, 2002

(86) PCT No.: PCT/SE02/00945

§ 371 (c)(1),
(2), (4) Date: Nov. 13, 2003

(87) PCT Pub. No.: WO02/094783

PCT Pub. Date: Nov. 28, 2002

(65) Prior Publication Data

US 2004/0152731 A1    Aug. 5, 2004

(30) Foreign Application Priority Data

May 18, 2001    (SE)    ..................... 0101770

(51) Int. Cl.
A61K 31/4468    (2006.01)
C07D 211/58    (2006.01)
(52) U.S. Cl. ...................... 514/326; 514/317; 546/192; 546/223
(58) Field of Classification Search ................ 514/326, 514/317; 546/192, 207
See application file for complete search history.

(56) References Cited

U.S. PATENT DOCUMENTS

| | | | |
|---|---|---|---|
| 4,091,096 A | 5/1978 | Beck et al. | |
| 4,126,689 A | 11/1978 | Sanczuk et al. | |
| 4,252,812 A | 2/1981 | Welch | |
| 4,460,586 A | 7/1984 | Berthold | |
| 4,680,296 A | 7/1987 | Manoury et al. | |
| 5,118,693 A | 6/1992 | Toth et al. | |
| 5,132,303 A | 7/1992 | Toth et al. | |
| 5,132,309 A | 7/1992 | Toth et al. | |
| 5,854,245 A | 12/1998 | Duggan et al. | |
| 6,153,626 A | 11/2000 | Pelcman et al. | |
| 6,399,635 B1 | 6/2002 | Pelcman et al. | |
| 6,455,545 B1 * | 9/2002 | Delorme et al. | 514/320 |
| 6,552,036 B1 * | 4/2003 | Boyd et al. | 514/299 |
| 6,556,387 B1 * | 4/2003 | Misso et al. | 360/265.6 |
| 6,756,387 B1 * | 6/2004 | Brown et al. | 514/318 |

FOREIGN PATENT DOCUMENTS

| | | |
|---|---|---|
| DE | 28 22 465 | 11/1978 |
| HU | 206 677 | 8/1989 |
| WO | WO 9828275 | * 2/1998 |
| WO | WO 98/28270 | 7/1998 |
| WO | WO 99/33806 | * 7/1998 |
| WO | WO 99/33806 | 7/1999 |
| WO | WO 99/45925 | 9/1999 |
| WO | WO 0146263 | 6/2001 |

OTHER PUBLICATIONS

Wei et al N, N-diethyl-4-(phenylpiperidin-4-ylidenemethyl)benzamide . . . J. Med. Chem. 2000, 43, 3895-3905.*

Bilsky, et al., SNC 80, A Selective, Nonpeptidic and Systemically Active Opioid Delta Agonist, J. Pharmacol. Experi. Ther. 273:359-366(1995).

Takemori, et al., "Selective Natrexone-Drived Opioid Receptor Antagonists," Annu. Rev. Pharmacol. Toxicol. 32:239-269 (1992).

Enein, et al., abstract #159379n, Synthesis of some 4-substituted amino-1-methyl piperidines structurally related to antihistaminics, Chem. Abstr. 78:396 (1973).

(Continued)

Primary Examiner—Rita Desai
(74) Attorney, Agent, or Firm—David Shen; Paul K. Legaard

(57) ABSTRACT

Compounds of general formula (I): $R^1$ is selected from any one of phenyl, pyridinyl, thienyl, furanyl, imidazolyl, pyrrolyl, triazolyl, thiazolyl and pyridine N-oxide; where each $R^1$ phenyl ring and $R^1$ heteroaromatic ring may optionally and independently be further substituted by 1, 2 or 3 substituents selected from straight and branched $C_1$–$C_6$ alkyl, $NO_2$, $CF_3$, $C_1$–$C_6$ alkoxy, chloro, fluoro, bromo, and iodo. The substitutions on the phenyl ring and on the heteroaromatic ring may take place in any position on said ring systems; are disclosed and claimed in the present application, as well as salts and pharmaceutical compositions comprising the novel compounds and their use in therapy, in particular in the management of pain, anxiety and functional gastrointestinal disorders.

(I)

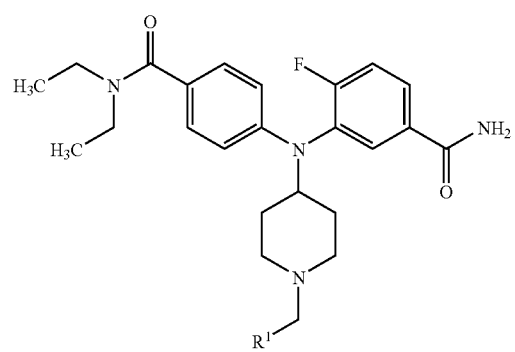

11 Claims, No Drawings

OTHER PUBLICATIONS

Laskowska, abstract #105299e, "1-methyl-r-[N-phenyl-N-(2-thienyl)amino]piperidine," Chem. Abstr. 81:510 (1974).

Podlogar, et al., "Synthesis and evaluation of 4-(N,N-diarylamino)piperidines with high selectivity to the o-opioid receptor: A combined 3D-QSAR and ligand docking study," Drug Design and Discovery, 34-50 (2000).

Sarges, et al., "Neuroleptic activity of chiral trans-hexahydro-y-carbvolines," J. Med. Chem. 29:8-19 (1986).

Database ChemABS 'Online', CAS, Columbus, Ohio, US; 1995, Wang, et al: "Opioid delta deceptor . . . and 4-(methoxymethyl)fentanyl)fentanyl", Database Accession No. 1995:857886.

Database ChemABS 'Online', CAS, Columbus, Ohio, US; Deruiter, et al: "Investigation of the synthesis . . . 1-substituted 4-(propanalilido)perhydroazepines", Database Accession No. 1992:612296.

Database ChemABS 'Online', CAS, Columbus, Ohio, US; Ferrand, et al: "Synthesis of New 1,2,3-triazin-4-ones as Potential Antidepressants", Database Accession No. 1988:150431.

Database ChemABS 'Online', CAS, Columbus, Ohio, US; Adachi, et al: "Aminohaloborane in organic synthesis. IX. Exclusive . . . N-monoaminoalkylanilines", Database Accession No. 1987:49715.

Database ChemABS 'Online', CAS, Columbus, Ohio, US; Takai, et al: "Synthesis and Pharmacological Evaluation . . . Heterocyclic Rings at the 4-position", Database Accession No. 1985:578235.

Database ChemABS 'Online', CAS, Columbus, Ohio, US; Sugasawa, et al: "I-Azacycloalkyl-I, 4-Benzodiazepin-2-ones with antianxiety- antidepressant actions", Database Accession No. 1985:437458.

Database ChemABS 'Online', CAS, Columbus, Ohio, US; ZHU, et al: "Studies on Potent Analgesics. I. Synthesis . . . Derivatives", Database Accession No. 1981:550311.

Database ChemABS 'Online', CAS, Columbus, Ohio, US; Burkartsmaier, et al: "Potential analgesics, IX: Synthesis . . . acid derivatives", Database Accession No. 1979:54780.

Database ChemABS 'Online', CAS, Columbus, Ohio, US; Obase, et al: "New antihypertensive agents. III. Synthesis and . . . at the 4-position", Database Accession No. 1984:120835.

* cited by examiner

4-(PHENYL-(PIPERIDIN-4-YL)-AMINO)-BENZAMIDE DERIVATIES AND THEIR USE FOR THE TREATMENT OF PAIN, ANXIETY OR GASTROINTESTINAL DISORDERS

CROSS-REFERENCE TO RELATED APPLICATIONS

This application is a U.S. National Stage of International Application No. PCT/SE02/00945 that was filed on May 16, 2002. The International Application claims priority under 35 U.S.C. § 119(a) to Swedish Application No. 0101770-6 filed May 18, 2001.

FIELD OF THE INVENTION

The present invention is directed to novel compounds, to a process for their preparation, their use and pharmaceutical compositions comprising the novel compounds. The novel compounds are useful in therapy, and in particular for the treatment of pain, anxiety and functional gastrointestinal disorders.

BACKGROUND OF THE INVENTION

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors (μ, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. One example of a non-peptidic δ-agonist is SNC80 (Bilsky E. J. et al., *Journal of Pharmacology and Experimental Therapeutics*, 273(1), pp. 359–366 (1995)). There is however still a need for selective δ-agonists having not only improved selectivity, but also an improved side-effect profile.

Thus, the problem underlying the present invention was to find new analgesics having improved analgesic effects, but also with an improved side-effect profile over current μ agonists, as well as having improved systemic efficacy.

Analgesics that have been identified and are existing in the prior art have many disadvantages in that they suffer from poor pharmacokinetics and are not analgesic when administered by systemic routes. Also, it has been documented that preferred δ agonist compounds, described within the prior art, show significant convulsive effects when administered systemically.

We have now found certain compounds that exhibit surprisingly improved properties, i.a. improved δ-agonist potency, in vivo potency, pharmacokinetic, bioavailability, in vitro stability and/or lower toxicity.

OUTLINE OF THE INVENTION

The novel compounds according to the present invention are defined by the formula I

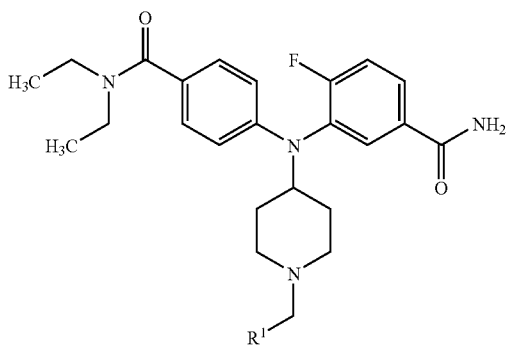

wherein
$R^1$ is selected from any one of
(i) phenyl;

(ii) pyridinyl

(iii) thienyl

(iv) furanyl

(v) imidazolyl

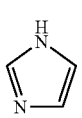

(vi) triazolyl

(vii) pyrrolyl

(viii) thiazolyl

(ix) pyridyl-N-oxide

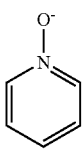

where each $R^1$ phenyl ring and $R^1$ heteroaromatic ring may optionally and independently be further substituted by 1, 2 or 3 substituents selected from straight and branched $C_1$–$C_6$ alkyl, $NO_2$, $CF_3$, $C_1$–$C_6$ alkoxy, chloro, fluoro, bromo, and iodo. The substitutions on the phenyl ring and on the heteroaromatic ring may take place in any position on said ring systems;

When the $R^1$ phenyl ring and the $R^1$ heteroaromatic ring(s) are substituted, the preferred substituents are selected from anyone of $CF_3$, methyl, iodo, bromo, fluoro and chloro.

A further embodiment of the present invention is a compound according to figure I wherein $R^1$ is as defined above and each $R^1$ phenyl ring and $R^1$ heteroaromatic ring may independently be further substituted by a methyl group A further embodiment of the present invention is a compound according to figure I wherein $R^1$ is phenyl, pyrrolyl, pyridinyl, thienyl or furanyl, optionally with 1 or 2 of the preferred substituents on the $R^1$ phenyl or $R^1$ heteroaromatic ring.

Another embodiment of the present invention is a compound according to figure I wherein $R^1$ is phenyl, pyrrolyl or pyridinyl, optionally with 1 or 2 of the preferred substituents on the $R^1$ phenyl or $R^1$ heteroaromatic ring.

Another embodiment of the present invention is a compound according to figure I wherein $R^1$ is thienyl or furanyl, optionally with 1 or 2 of the preferred substituents on the $R^1$ heteroaromatic ring.

Within the scope of the invention are also salts and enantiomers of the compounds of the formula I, including salts of enantiomers.

Reaction step b in Scheme 1, vide infra, is performed by reacting an intermediate compound of the general formula II

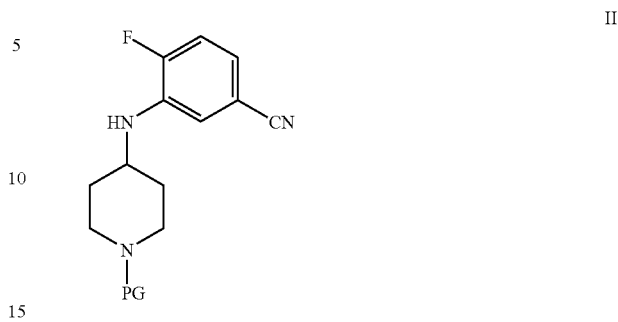

II wherein PG is a urethane protecting group, such as Boc and CBZ, or benzyl or substituted benzyl protecting group, such as 2,4-dimethoxybenzyl; with N,N-diethyl-4-bromobenzamide, using a palladium catalyst, e.g. tris(dibenzylideneacetone) dipalladium(0)-[$Pd_2(dba)_3$], in the presence of a base, e.g. tert-BuONa and a phosphine ligand such as bis-diphenylphosphanyl-dimethyl-9H-xanthene (xantphos), to give the compounds of general formula III,

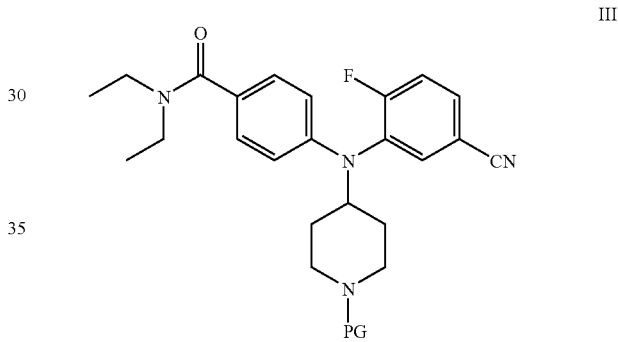

III which is thereafter 1) deprotected, under standard conditions, 2) hydrolyzed under basic conditions and 3) alkylated using either:

i) a compound of the general formula $R^1$—$CH_2$—X, wherein $R^1$ is as defined above and X is a halogen, preferably bromine or chlorine and a suitable base, or ii) a compound of the general formula $R^1$—CHO, wherein $R^1$ is as defined above, and a suitable reducing agent, to give compounds of the general formula I.

Suitable bases to be used in the standard alkylation step i) above include, but are not limited to, triethylamine and potassium carbonate.

Suitable reducing agents to be used in the standard reduction step ii) include, but are not limited to, sodium cyanoborohydride and sodium triacetoxyborohydride.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labeled versions of the compounds of the invention in diagnostic techniques and imaging applications such as positron emission tomography (PET).

Compounds of the invention are useful for the treatment of diarrhoea, depression, anxiety and stress-related disorders such as post-traumatic stress disorders, panic disorder, generalized anxiety disorder, social phobia, and obesessive compulsive disorder; urinary incontinence, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (eg. amnesia, analgesia, muscle relaxation and sedation). Included in this combination are inhaled anaesthetics, hypnotics, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

A further aspect of the present invention is intermediates of the general formula II and III,

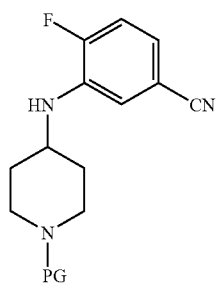

II

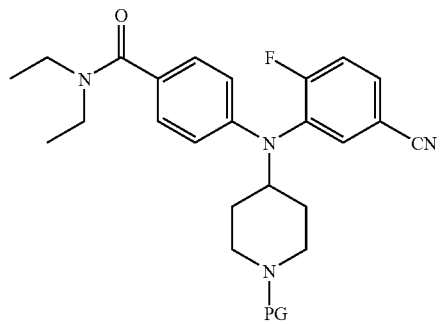

III wherein PG is a urethane protecting group, such as Boc and CBZ or benzyl or substituted benzyl protecting group, such as 2,4-dimethoxybenzyl.

A further embodiment of the present invention is intermediates of the Formula X

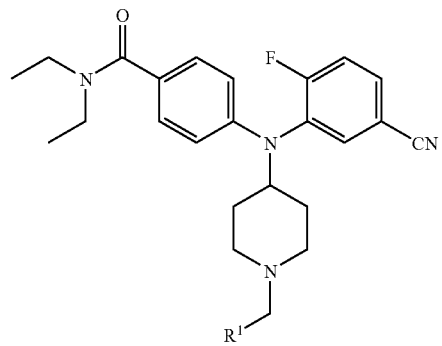

X wherein $R^1$ is as described above in relation to Formula I.

In another alternative synthetic route, reaction step b in Scheme 2, vide infra, is performed by reacting an intermediate compound of the general formula IV

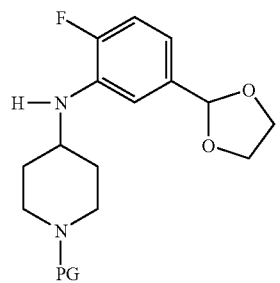

IV wherein PG is a urethane or benzyl-like protecting group, such as Boc, N,N-diethyl-4-bromobenzamide, using a palladium catalyst, e.g. tris(dibenzylideneacetone) dipalladium (0) [Pd$_2$(dba)$_3$], in the presence of a base, e.g. tert-BuONa and a phosphine ligand such as bis-diphenylphosphanyl-dimethyl-9H-xanthene (xantphos), to give the compounds of general formula V,

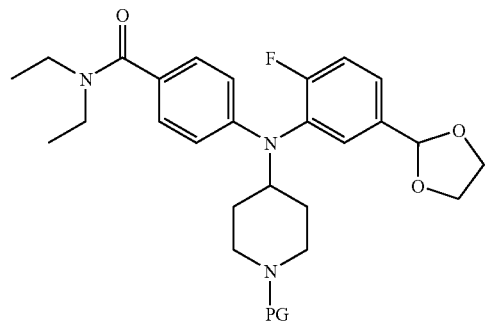

V which is thereafter 1) deprotected, under standard conditions, 2) hydrolyzed under basic conditions and 3) alkylated using either:

i) a compound of the general formula $R^1$—$CH_2$—X, wherein $R^1$ is as defined above and X is a halogen, preferably bromine or chlorine and a suitable base, or ii) a compound of the general formula $R^1$—CHO, wherein $R^1$ is as defined above, and a suitable reducing agent, to give compounds of the general formula I.

This is followed by conversion of the ketal functionality to a primary amide under standard conditions via 1) hydrolysis of the ketal to the aldehyde (formula VI), followed by 2) oxidation of the aldehyde to the corresponding carboxylic acid (formula VII), followed by 3) amidation with ammonium chloride to the primary amide giving compounds of the general formula I.

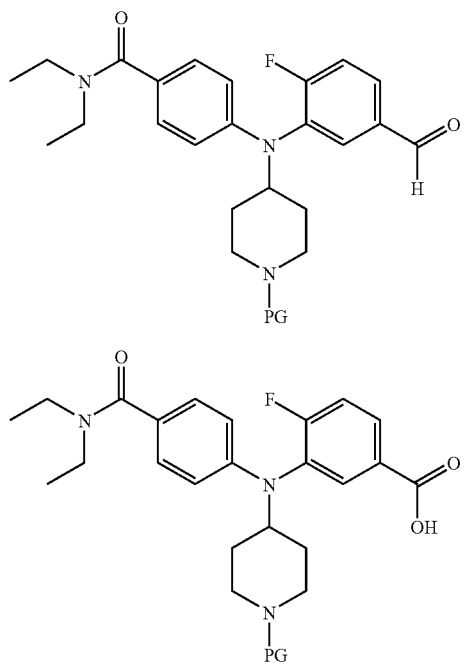

VI

VII

Suitable hydrolysis conditions to be used in the standard hydrolysis step (i) include, but are not limited to aqueous hydrochloric acid in tetrahydrofuran.

Suitable conditions for the oxidation step (ii) include, but are not limited to stirring at 0° C. in aqueous sodium dihydrogen phosphate and sodium chlorite in the presence of excess 2-methyl-2-butene.

Suitable conditions for the amidation step (iii) include but are not limited to treatment with excess ammonium chloride in the presence of a coupling agent such as benzotriazole-1-yloxy-trisphosphonium hexafluorophosphate (hereinafter Py-BOP).

Methods of Preparation

EXAMPLES

The invention will now be described in more detail by the following Schemes and Examples, which are not to be construed as limiting the invention.

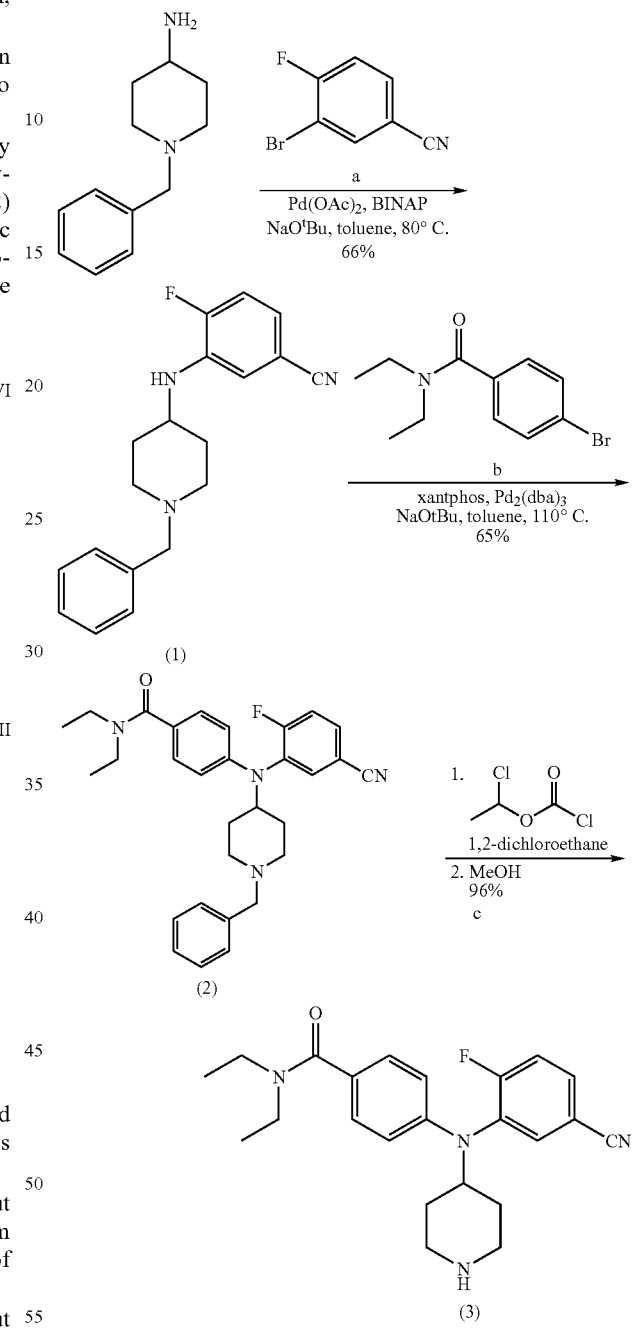

Scheme 1: Synthesis of Intermediate Amine (compound 3) Used in Reductive Aminations Method 1A (Compound 1): 3-(1-Benzyl-piperidin-4-ylamino)-4-fluoro-benzonitrile.

To a dry flask containing 3-bromo-4-fluoro benzonitrile (6.56 g, 1 eq) was added dry toluene (100 mL), 4-amino-1-benzyl piperidine (1.2 eq), racemic BINAP (612 mg, 0.03 eq), palladium acetate (220 mg, 0.02 eq) and sodium tert-butoxide (4.4 g, 1.4 eq). The reaction was heated to 80° C. under and inert atmosphere for 20 hours. The reaction was cooled, diluted with ethyl acetate (200 mL) and washed with water (100 mL). The combined organics were dried (MgSO₄), filtered and concentrated. Purification by flash chromatography, eluting 3% methanol in dichloromethane yielded amine (1) as a yellow solid (6.655 g, 66%).

Method 1B (Compound 2): [(1-Benzyl-piperidin-4-yl)-(5-cyano-2-fluoro-phenyl)-amino]-N,N-diethyl-benzamide.

To a solution of amine (1) (3.50 g, 1 eq.) in dry toluene (50 mL) was added aryl bromide (4.35 g, 1.5 eq), xantphos (393 mg, 0.06 eq), Pd₂(dba)₃ (331 mg, 0.03 eq) and sodium tert-butoxide (1.52 g, 1.4 eq). The reaction was heated to reflux for 14 hours then was cooled and diluted with ethyl acetate (100 mL). The solution was washed with water (100 mL) then the organics were dried (MgSO₄), filtered and concentrated. Purification by flash chromatography, eluting 65% ethyl acetate 35% hexanes, rising to 70% ethyl acetate 30% hexanes yielded amine (2) as an orange oil (3.568 g, 65% yield).

Method 1C (Compound 3): [(5-Cyano-2-fluoro-phenyl)-piperidin-4-yl-amino]-N,N-diethyl-benzamide.

To a solution of amine (2) (3.564 g, 1 eq) in 1,2-dichloroethane (65 mL) at 0° C. was added 1-chloroethyl chloroformate (920 μL, 1.15 eq). After 1 hour at 0° C. the reaction was warmed to room temperature then was heated to 70° C. for 90 minutes. The reaction was then cooled and concentrated. The residue was dissolved in methanol (60 mL) then heated to 70° C. for 1 hour. The solution was then cooled and concentrated. Purification by flash chromatography, eluting 10% methanol in dichloromethane, rising to 40% methanol in dichloromethane gave amine as a yellow foam (2.786 g, 96%).

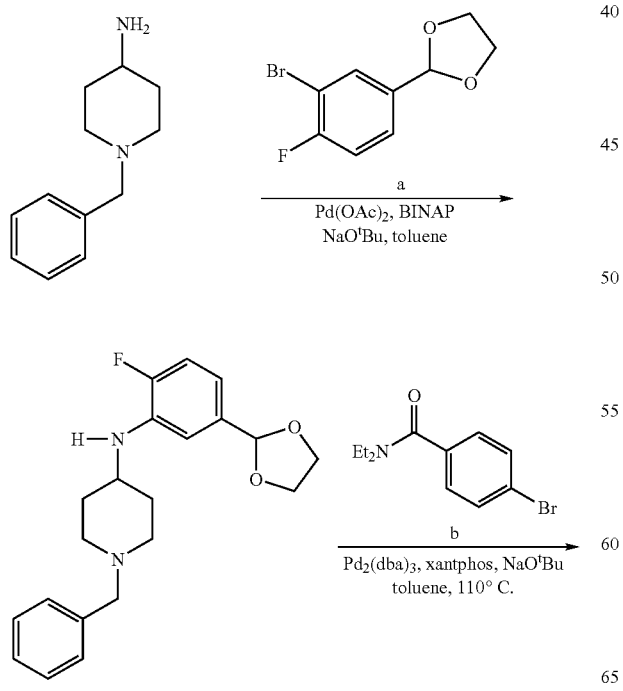

Scheme 2:
Alternative synthesis Via Intermediate 7

4

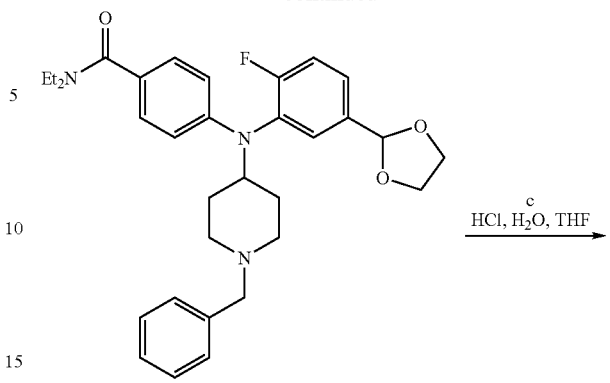

5

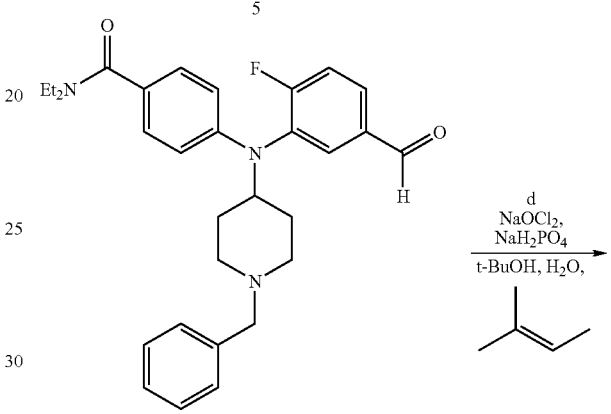

6

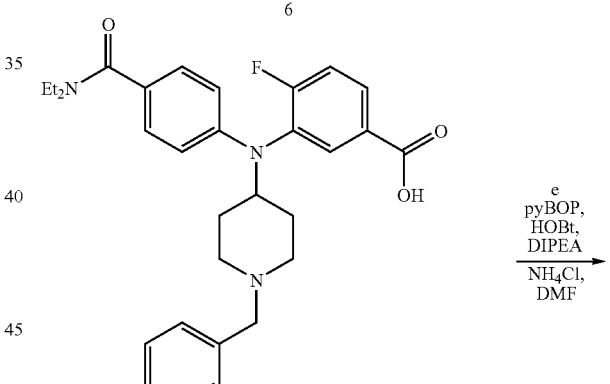

7

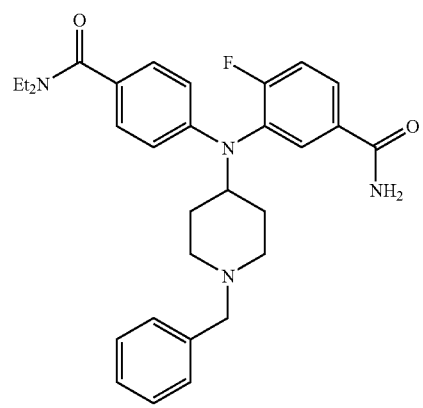

Example 1

Intermediate 4: (1-Benzyl-piperidin-4-yl)-(5-[1,3]dioxolan-2-yl-2-fluoro-phenyl)-amine.

To a dry flask containing 2-(3-bromo-4-fluorophenyl)-1,3-dioxaolane (1.0 eq) and amine, (1.2 eq) in dry toluene is added BINAP (0.03 eq), palladium acetate (0.02 eq) and sodium tert-butoxide (1.4 eq). The reaction is heated to 80° C. under nitrogen. After about 24 hours the solution is cooled, diluted with ethyl acetate and washed with one portion water. The organics are dried over anhydrous magnesium sulfate, filtered and concentrated. The residue is purified by flash chromatography, eluting with a methanol in dichloromethane gradient.

Intermediate 5: [(1-Benzyl-piperidin-4-yl)-(5-[1,3]dioxolan-2-yl-2-fluoro-phenyl)-amino]-N,N-diethyl-benzamide.

To a dry flask containing amine 4 in dry toluene (about 6 mL per millimole of 4) is added aryl bromide (1.4 eq), xantphos (0.06 eq), Pd$_2$(dba)$_3$ (0.03 eq) and sodium tert-butoxide (1.4 eq). The reaction is heated to 110° C. under nitrogen. After about 24 hours the solution is cooled, diluted with ethyl acetate and washed with one portion water. The organics are dried over anhydrous magnesium sulfate, filtered and concentrated. The residue is purified by flash chromatography, eluting with a methanol in dichloromethane gradient.

Intermediate 6: [(1-Benzyl-piperidin-4-yl)-(2-fluoro-5-formyl-phenyl)-amino]-N,N-diethyl-benzamide.

To a solution of acetal 5 in tetrahydrofuran is added 2N HCl solution (2.0 eq). After 16 hours at room temperature, dichloromethane is added and the aqueous layer is neutralized with aqueous saturated sodium bicarbonate solution. The organic layer is removed and the aqueous layer extracted with two portions of dichloromethane. The combined organic extracts are dried (MgSO$_4$), filtered and concentrated and the residue is purified by flash chromatography, eluting with an ethyl acetate in hexanes gradient.

Intermediate 7: [(1-Benzyl-piperidin-4-yl)-(4-diethylcarbamoyl-phenyl)-amino]-4-fluoro-benzoic acid.

To a solution of aldehyde 6 (1.0 eq) in tert-butanol is added 2-methyl-2-butene (10.0 eq) and the solution is cooled to 0° C. A solution of sodium dihydrogen phosphate (9 eq) and sodium chlorite (9 eq) in water is added and the reaction is stirred for 30 minutes at 0° C. The tert-butanol is removed and the reaction mixture is extracted with dichloromethane. The combined organic extracts are dried (MgSO$_4$), filtered and concentrated and the residue is purified by flash chromatography, eluting with a methanol/dichloromethane gradient.

Example 1

[(1-Benzyl-piperidin-4-yl)-(4-diethylcarbamoyl-phenyl)-amino]-4-fluoro-benzamide (Alternative Synthesis)

To a solution of acid 7 (1.0 eq) in DMF is added pyBOP (1.5 eq); HOBt (1.5 eq), diisopropylethylamine (4.0 eq) and ammonium chloride (2 eq). After 16–24 hours at room temperature the reaction is concentrated. The residue is dissolved in ethyl acetate and is washed with two portions of water and one portion of saturated sodium bicarbonate solution. The organic layer is dried (MgSO$_4$), filtered and concentrated and the residue is purified by flash chromatography, eluting with a methanol in dichloromethane gradient.

Additional examples were synthesized via the general procedures described below.

A. Reductive Amination of Intermediate 3:

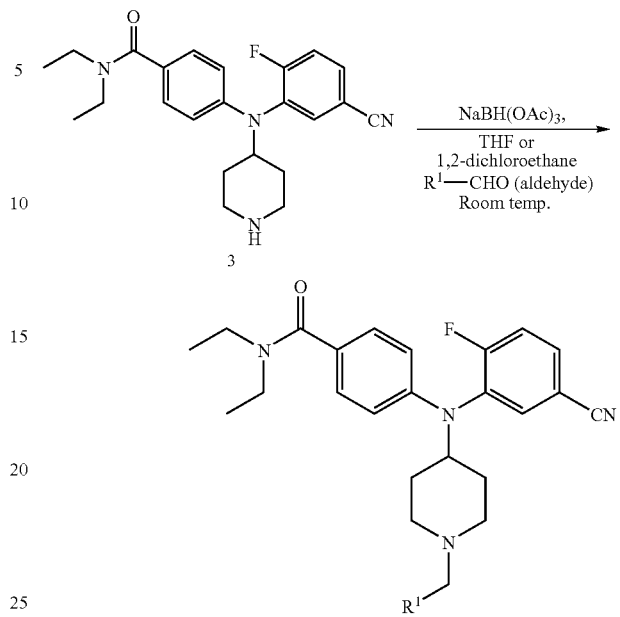

To a solution of the amine, 3, in dry tetrahydrofuran (THF) or 1,2-dichloroethane is added the aldehyde (1–1.5 eq.), followed by sodium triacetoxyborohydride (1–1.6 eq.). The reaction is stirred at room temperature under a nitrogen atmosphere for an extended period of time (6–48 hours) to ensure complete reaction. The reaction mixture is then subjected to a standard work-up procedure and a standard purification. The amount of THF or 1,2-dichloroethane is not crucial. An amount corresponding to about 1 mL/30 mg is preferred.

Procedure 2A in the synthesis of Example 2 below is typical.

B. Hydrolysis of the Intermediate Cyano Compound:

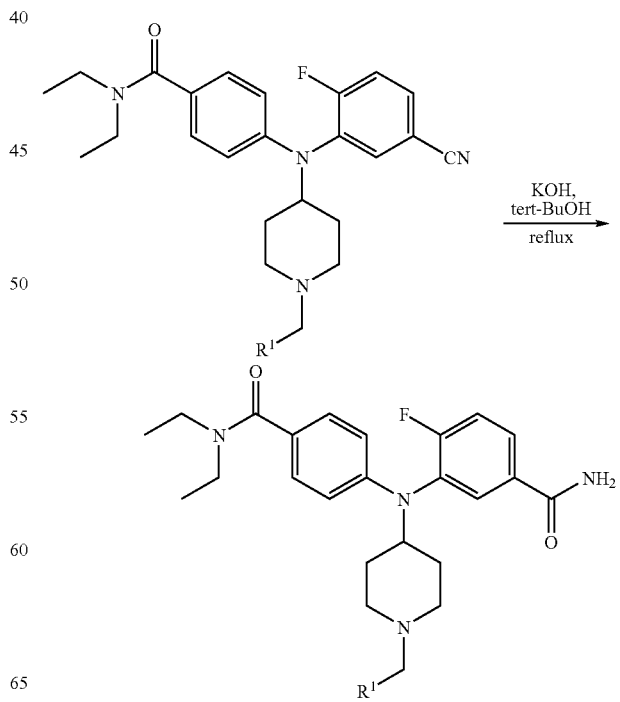

To a solution of the cyano intermediate in tert-butanol, is added ground potassium hydroxide (KOH) (2.5 eq.) and the resulting mixture is heated to reflux for about two hours. The mixture was then cooled to room temperature and subjected to a standard work-up procedure and a standard purification. The amount of tert-butanol is not crucial. An amount corresponding to about 1 mL/30 mg is preferred.

Procedure 2B in the synthesis of Example 2 below is typical.

Example 2

[(4-Diethylcarbamoyl-phenyl)-(1-pyridin-2-ylmethyl-piperidin-4-yl)-amino]-4-fluoro-benzamide 2B: [(4-Diethylcarbamoyl-phenyl)-(1-pyridin-2-ylmethyl-piperidin-4-yl)-amino]-4-fluoro-benzamide.

To a solution of nitrile (317 mg) in tert-butanol (10 mL) was added ground potassium hydroxide (92 mg; 2.5 eq) and the reaction was heated to reflux. After 90 minutes the solution was cooled, diluted with dichloromethane and washed with one portion water. The organics was removed and the aqueous neutralized with 2M hydrochloric acid and extracted with two portions dichloromethane. The combined organics were dried over anhydrous magnesium sulfate, filtered and concentrated. The residue was purified by flash chromatography eluting with 5% methanol in dichloromethane, rising to 7% methanol in dichloromethane. A

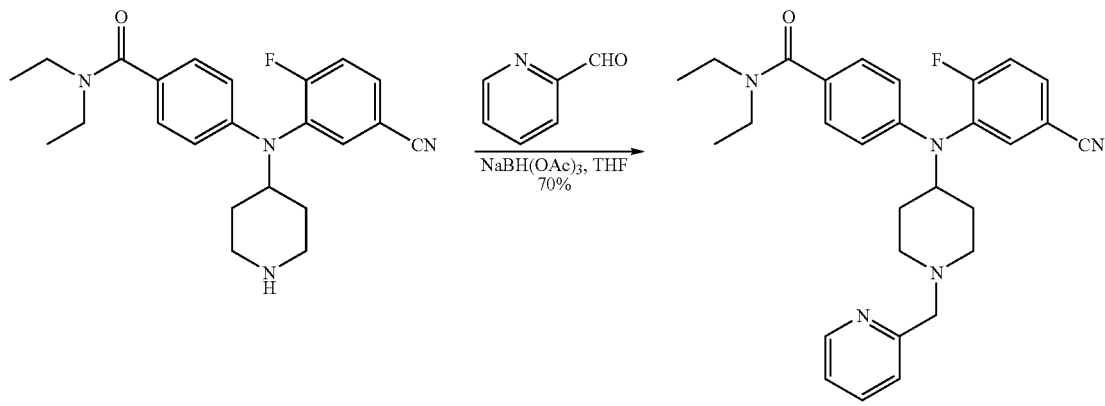

colorless foam was obtained (164.0 mg; 50% yield). The foam was dissolved in ether (8 mL) containing some dichloromethane and 1N HCl/ether (1.0 mL; ≅3.0 eq) was added After 1 hour the solution was concentrated and the solid dried under high vacuum.

Additional Examples are prepared analogously. Analytical data for synthetic Examples is shown in Table 1, on the following pages.

2A: [(5-Cyano-2-fluoro-phenyl)-(1-pyridin-2-ylmethyl-piperidin-4-yl)-amino]-N,N-diethyl-benzamide.

To a solution of amine (370 mg) in dry tetrahydrofuran (10 mL) was added pyridine-2-carboxaldehyde (116 μL; 1.3 eq) and sodium triacetoxyborohydride (279 mg; 1.4 eq). The reaction was stirred at room temperature under nitrogen. After 24 hours the reaction was diluted with dichloromethane and washed with saturated aqueous sodium bicarbonate. The aqueous was extracted with two portions dichloromethane and the combined organics were dried over anhydrous magnesium sulfate, filtered and concentrated. The residue was purified by flash chromatography eluting 4% methanol in dichloromethane. A colorless foam was obtained (317.5 mg; 70% yield).

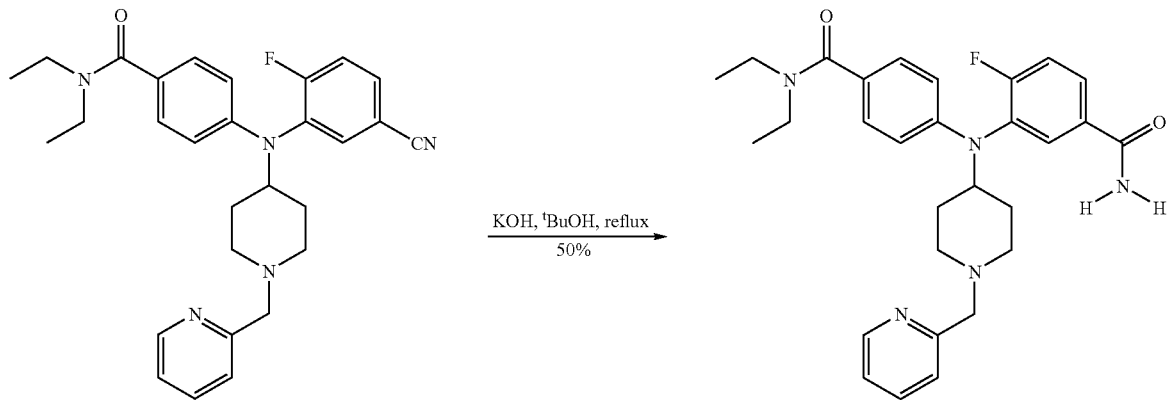

TABLE 1

Analytical data for synthetic Examples

| Ex. # | R¹ | Name | NMR data(400 MHz, CD₃OD) |
|---|---|---|---|
| 1 | phenyl | [(1-Benzyl-piperidin-4-yl)-(4-diethylcarbamoyl-phenyl)-amino]-fluoro-benzamide | (1.19(br s, 6H, CH₃); 1.69–1.80(m, 2H, CH₂); 2.31(d, J=14Hz, 2H, CH₂); 3.25–3.55(m, 8H, NCH₂); 4.31(s, 2H, NCH₂Ar); 4.42–4.49 (m, 1H, NCH); 6.70(d, J=9Hz, 2H, Ar—H); 7.26(d, J=9Hz, 2H, Ar—H); 7.38–7.42(m, 1H, Ar—H); 7.47–7.51(m, 5H, Ar—H); 7.83(dd, J=3, 7.5Hz, 1H, Ar—H); 7.99–8.03(m, 1H, Ar—H). |
| 2 | pyridin-2-yl | [(4-Diethylcarbamoyl-phenyl)-(1-pyridin-2-ylmethyl-piperidin-4-yl)-amino]-fluoro-benzamide | 1.17(br s, 6H, CH3); 1.81–1.85(m, 2H, CH₂); 2.31(d, J=14Hz, 2H, CH₂); 3.36–3.42(m, 6H, NCH₂); 3.63(d, J=12Hz, 2H, NCH₂); 4.48–4.52(m, 3H, NCH2 and NCH); 6.70(d, J=8.5Hz, 2H, Ar—H); 7.26(d, J=8.5Hz, 2H, Ar—H); 7.41(t, J=8.5Hz, 1H, Ar—H); 7.51–7.54(m, 1H, Ar—H); 7.60(d, J=7.5Hz, 1H, Ar—H); 7.84–7.86(m, 1H, Ar—H); 7.98–8.01 (m, 2H, Ar—H); 8.68(d, J=6.5Hz, 1H, Ar—H). |
| 3 | thiophen-3-yl | [(4-Diethylcarbamoyl-phenyl)-(1-thiophen-3-ylmethyl-piperidin-4-yl)-amino]-fluoro-benzamide | 1.16(br s, 6H, CH₃); 1.63–1.74(m, 2H, CH₂); 2.31(d, J=14Hz, 2H, CH₂); 3.19–3.25(m, 2H, NCH₂); 3.40(br s, 4H, NCH2); 3.52(d, J=13Hz, 2H, NCH₂); 4.31(s, 2H, NCH₂Ar); 4.36–4.45(m, 1H, NCH); 6.67(d, J=9.5Hz, 2H, Ar—H); 7.18–7.27(m, 3H, Ar—H); 7.38(t, J=9Hz, 1H, Ar—H); 7.54–7.56(m, 1H, Ar—H); 7.65–7.66(m, 1H, Ar—H); 7.81(dd, J=2, 7.5Hz, 1H, Ar—H); 7.97–8.01(m, 1H, Ar—H). |
| 4 | furan-3-yl | [(4-Diethylcarbamoyl-phenyl)-(1-furan-3-ylmethyl-piperidin-4-yl)-amino]-fluoro-benzamide | 1.16(br s, 6H, CH₃); 1.57–1.67(m, 2H, CH₂); 2.32(d, J=14Hz, 2H, CH₂); 3.17–3.23(m, 2H, NCH₂); 3.42(br s, 4H, NCH₂); 3.56(d, J=12Hz, 2H, NCH₂); 4.18(s, 2H, NCH₂Ar); 4.39–4.45(m, 1H, NCH); 6.56(s, 1H, Ar—H); 6.67(d, J=9.5Hz, 2H, Ar—H); 7.23–7.27(m, 2H, Ar—H); 7.39(t, J=9.5Hz, 1H, Ar—H); 7.61 (t, J=2Hz, 1H, Ar—H); 7.74(s, 1H, Ar—H); 7.81(dd, J=2.5, 7.5Hz, 1H, Ar—H); 7.97–8.01 (m, 1H, Ar—H) |
| 5 | thiophen-2-yl | [(4-Diethylcarbamoyl-phenyl)-(1-thiophen-2-ylmethyl-piperidin-4-yl)-amino]-fluoro-benzamide | 1.16(br s, 6H, CH₃); 1.63–1.74(m, 2H, CH₂); 2.33(d, J=14Hz, 2H, CH₂); 3.24(t, J=11Hz, 2H, NCH₂); 3.40(br s, 4H, NCH₂); 3.57(d, J=12Hz, 2H, NCH2); 4.39–4.45(m, 1H, NCH); 4.54(s, 2H, NCH₂Ar); 6.67(d, J=9.5Hz, 2H, Ar—H); 7.11–7.13(m, 1H, Ar—H); 7.22–7.26(m, 2H, Ar—H); 7.31(d, J=3.5Hz, 1H, Ar—H); 7.39(t, J=9.5Hz, 1H, Ar—H); 7.61(d, J=6.5Hz, 1H, Ar—H); 7.80–7.82(m, 1H, Ar—H); 7.97–8.01(m, 1H, Ar—H). |
| 6 | 2,4-dichlorophenyl | [[1-(2,4-Dichloro-benzyl)-piperidin-4-yl]-(4-diethylcarbamoyl-phenyl)-amino]-fluoro-benzamide | 1.16(br s, 6H, CH₃); 1.67–1.77(m, 2H, CH₂); 2.31(d, J=14Hz, 2H, CH₂); 3.30–3.50(m, 6H, NCH₂); 3.59(d, J=12Hz, 2H, NCH₂); 4.42–4.48(m, 3H, NCH and NCH₂Ar); 6.67 (d, J=9.5Hz, 2H, Ar—H); 7.23(d, J=8.5Hz, 2H, Ar—H); 7.38(t, J=9.5Hz, 1H, Ar—H); 7.45–7.48(m, 1H, Ar—H); 7.59(d, J=8.5Hz, 1H, Ar—H); 7.66(d, J=2Hz, 1H, Ar—H); 7.80 (J=2, 7.5Hz, 1H, Ar—H); 7.96–8.00(m, 1H, Ar—H). |
| 7 | thiazol-2-yl | [(4-Diethylcarbamoyl-phenyl)-(1-thiazol-2-ylmethyl-piperidin-4-yl)-amino]-fluoro-benzamide | 1.16(br s, 6H, CH₃); 1.77–1.82(m, 2H, CH₂); 2.33(d, J=14Hz, 2H, CH₂); 3.40–3.53(m, 6H, NCH₂); 3.71(d, J=11Hz, 2H, NCH₂); 4.48–4.53(m, 1H, NCH); 4.73(s, 2H, NCH₂Ar); 6.73(d, J=8.5Hz, 2H, Ar—H); 7.30 (d, J=8.5Hz, 2H, Ar—H); 7.39–7.43(m, 1H, Ar—H); 7.77(d, J=3Hz, 1H, Ar—H); 7.84(d, J=5.5Hz, 1H, Ar—H); 7.93(d, J=3Hz, 1H, Ar—H); 8.00–8.04(m, 1H, Ar—H). |

TABLE 1-continued

Analytical data for synthetic Examples

| Ex. # | R¹ | Name | NMR data(400 MHz, CD$_3$OD) |
|---|---|---|---|
| 8 | 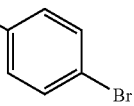 | [[1-(4-Bromo-benzyl)-piperidin-4-yl]-(4-diethylcarbamoyl-phenyl)-amino]-fluoro-benzamide | 1.16(br s, 6H, CH$_3$); 1.64–1.75(m, 2H, CH$_2$); 2.30(d, J=14Hz, 2H, CH2); 3.22–3.28(m, 2H, NCH$_2$); 3.42–3.53(m, 6H, NCH$_2$); 4.27 (s, 2H, NCH$_2$Ar); 4.38–4.46(m, 1H, NCH); 6.67(d, J=8.5Hz, 2H, Ar—H); 7.24(d, J=8.5Hz, 2H, Ar—H); 7.36–7.41(m, 3H, Ar—H); 7.63(d, J=8.5Hz, 2H, Ar—H); 7.80(dd, J=2, 7.5Hz, 1H, Ar—H); 7.97–8.00(m, 1H, Ar—H). |
| 9 |  | [(4-Diethylcarbamoyl-phenyl)-(1-furan-2-ylmethyl-piperidin-4-yl)-amino]-fluoro-benzamide | 1.16(br s, 6H, CH$_3$); 1.63–1.73(m, 2H, CH$_2$); 2.32(d, J=14Hz, 2H, CH$_2$); 3.22–3.48(m, 6H, NCH$_2$); 3.53(d, J=13Hz, 2H, NCH$_2$); 4.37(s, 2H, NCH$_2$Ar); 4.39–4.44(m, 1H, NCH); 6.50–6.52(m, 1H, Ar—H); 6.65–6.70 (m, 3H, Ar—H); 7.21(d, J=3Hz, 2H, Ar—H); 7.39(t, J=9.5Hz, 1H, Ar—H); 7.65(s, 1H, Ar—H); 7.81(dd, J=2, 7.5Hz, 1H, Ar—H); 7.90–8.01(m, 1H, Ar—H). |
| 10 |  | [(4-Diethylcarbamoyl-phenyl)-(1-pyridin-4-ylmethyl-piperidin-4-yl)-amino]-fluoro-benzamide | 1.16(br s, 6H, CH$_3$); 1.85–1.94(m, 2H, CH$_2$); 2.31(d, J=13Hz, 2H, CH$_2$); 3.30–3.48(m, 6H, NCH$_2$); 3.60(d, J=11Hz, 2H, NCH$_2$); 4.45–4.51(m, 1H, NCH); 4.68(s, 2H, NCH$_2$Ar); 6.69(d, J=8.5Hz, 2H, Ar—H); 7.24 (d, J=9.5Hz, 2H, Ar—H); 7.38(t, J=9.5Hz, 1H, Ar—H); 7.82(d, J=6.5Hz, 1H, Ar—H); 7.97–8.01(m, 1H, Ar—H); 8.32(d, J=7.5Hz, 2H, Ar—H); 8.98(d, J=6.5Hz, 2H, Ar—H). |
| 11 | 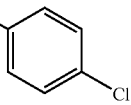 | [[1-(4-Chloro-benzyl)-piperidin-4-yl]-(4-diethyl-carbamoyl-phenyl)-amino]-fluoro-benzamide | 1.14(br s, 6H, CH$_3$); 1.62–1.73(m, 2H, CH$_2$); 2.28(d, J=15Hz, 2H, CH$_2$); 3.23(t, J=13Hz, 2H, NCH$_2$); 3.39(br s, 4H, NCH$_2$); 3.50(d, J=13Hz, 2H, NCH$_2$); 4.26(s, 2H, NCH$_2$Ar); 4.36–4.44(m, 1H, NCH); 6.64(d, J=8.5Hz, 2H, Ar—H); 7.20(d, J=9.5Hz, 2H, Ar—H); 7.36 (t, J=9.5Hz, 1H, Ar—H); 7.42–7.47(m, 4H, Ar—H); 7.78(dd, J=2, 7.5Hz, 1H, Ar—H); 7.94–7.98(m, 1H, Ar—H). |
| 12 |  | [(4-Diethylcarbamoyl-phenyl)-(1-pyridin-3-ylmethyl-piperidin-4-yl)-amino]-fluoro-benzamide | 1.15(br s, 6H, CH$_3$); 1.80(q, J=12Hz, 2H, CH$_2$); 2.29(d, J=14Hz, 2H, CH$_2$); 3.35–3.47 (m, 6H, NCH$_2$); 3.60(d, J=12Hz, 2H, NCH$_2$); 4.42–4.49(m, 1H, NCH); 4.60(s, 2H, NCH$_2$Ar); 6.66(d, J=8.5Hz, 2H, Ar—H); 7.22 (d, J=8.5Hz, 2H, Ar—H); 7.35(t, J=9.5Hz, 1H, Ar—H); 7.79(d, J=6.5Hz, 1H, Ar—H); 7.94–7.98(m, 1H, Ar—H); 8.11–8.15(m, 1H, Ar—H); 8.78(d, J=8.5Hz, 1H, Ar—H); 8.94(d, J=5.5Hz, 1H, Ar—H); 9.14(s, 1H, Ar—H). |
| 13 | 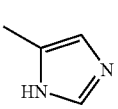 | {(4-Diethylcarbamoyl-phenyl)-[1-(3H-imidazol-4-ylmethyl-piperidin-4-yl]-amino}-fluoro-benzamide | 1.14(br s, 6H, CH$_3$); 1.79–1.85(m, 2H, CH$_2$); 2.31(d, J=14Hz, 2H, CH$_2$); 3.32–3.46(m, 6H, NCH$_2$); 3.60(d, J=11Hz, 2H, NCH$_2$); 4.41–4.47(m, 1H, NCH); 4.50(s, 2H, NCH$_2$Ar); 6.67(d, J=9.5Hz, 2H, Ar—H); 7.22(d, J=8.5Hz, 2H, Ar—H); 7.36(t, J=9.5Hz, 1H, Ar—H); 7.80 (d, J=5.5Hz, 1H, Ar—H); 7.86(s, 1H, Ar—H); 7.95–7.99(m, 1H, Ar—H); 9.05(d, J=2Hz, 1H, Ar—H). |
| 14 | 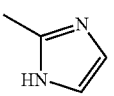 | {(4-Diethylcarbamoyl-phenyl)-[1-(1H-imidazol-2-ylmethyl)-piperidin-4-yl]-amino}-fluoro-benzamide | 1.14(br s, 6H, CH$_3$); 1.79–1.85(m, 2H, CH$_2$); 2.31(d, J=14Hz, 2H, CH$_2$); 3.32–3.46(m, 6H, NCH$_2$); 3.60(d, J=11Hz, 2H, NCH$_2$); 4.41–4.47(m, 1H, NCH); 4.50(s, 2H, NCH$_2$Ar); 6.67(d, J=9.5Hz, 2H, Ar—H); 7.22(d, J=8.5Hz, 2H, Ar—H); 7.36(t, J=9.5Hz, 1H, Ar—H); 7.80 (d, J=5.5Hz, 1H, Ar—H); 7.86(s, 1H, Ar—H); 7.95–7.99(m, 1H, Ar—H); 9.05(d, J=2Hz, 1H, Ar—H). |

TABLE 1-continued

Analytical data for synthetic Examples

| Ex. # | R¹ | Name | NMR data(400 MHz, CD₃OD) |
|---|---|---|---|
| 15 |  | {(4-Diethylcarbamoyl-phenyl)-[1-(1H-pyrrol-2-ylmethyl)-piperidin-4-yl]-amino}-fluoro-benzamide | 1.13(br s, 6H, CH₃); 1.58–1.69(m, 2H, CH₂); 2.29(d, J=13Hz, 2H, CH₂); 3.10(d, J=11Hz, 1H, NCH); 3.14(d, J=11Hz, 1H, NCH); 3.38 (br s, 4H, NCH₂); 3.47(d, J=13Hz, 2H, NCH₂); 4.21(s, 2H, NCH₂Ar); 4.31–4.39(m, 1H, NCH); 6.12(m, 1H, Ar—H); 6.29(s, 1H, Ar—H); 6.63 (d, J=8.5Hz, 2H, Ar—H); 6.83–6.84(m, 1H, Ar—H); 7.20(d, J=9Hz, 2H, Ar—H); 7.35(t, J=9.5Hz, 1H, Ar—H); 7.77–7.79(m, 1H, Ar—H); 7.94–7.98(m, 1H, Ar—H); 10.60(br s, 1H, NH) |

Pharmaceutical Compositions

The novel compounds according to the present invention may be administered orally, sublingually, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly. The dosage will depend on the route of administration, the severity of the disease, age and weight of the patient and other factors normally considered by the attending physician, when determining the individual regimen and dosage level as the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Salts include, but are not limited to, pharmaceutically acceptable salts. Examples of pharmaceutically acceptable salts within the scope of the present invention include: acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, and benzathine.

Examples of pharmaceutically unacceptable salts within the scope of the present invention include: hydroiodide, perchlorate, tetrafluoroborate. Pharmaceutically unacceptable salts could be of use because of their advantageous physical and/or chemical properties, such as crystallinity.

Preferred pharmaceutically acceptable salts are hydrochlorides, sulfates and bitartrates. The hydrochloride and sulfate salts are particularly preferred.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Biological Evaluation

In vitro Model

Cell Culture

A. Human 293S cells expressing cloned human μ, δ, and κ receptors and neomycin resistance were grown in suspension at 37° C. and 5% $CO_2$ in shaker flasks containing calcium-free DMEM10% FBS, 5% BCS, 0.1% Pluronic F-68, and 600 μg/ml geneticin.

B. B. Mouse and rat brains were weighed and rinsed in ice-cold PBS (containing 2.5 mM EDTA, pH 7.4). The brains were homogenized with a polytron for 15 sec (mouse) or 30 sec (rat, in ice-cold lysis buffer (50 mM Tris, pH 7.0, 2.5 mM EDTA, with phenylmethylsulfonyl fluoride added just prior use to 0.5MmM from a 0.5M stock in DMSO:ethanol).

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g (max) for 30 min. The pellets were resuspended in cold Tris buffer (50 mM Tris/Cl, pH 7.0) and spun again. The final pellets were resuspended in membrane buffer (50 mM Tris, 0.32 M sucrose, pH 7.0). Aliquots (1 ml) in polypropylene tubes were frozen in dry ice/ethanol and stored at −70° C. until use. The protein concentrations were determined by a modified Lowry assay with SDS.

Binding Assays

Membranes were thawed at 37° C., cooled on ice, passed 3 times through a 25-gauge needle, and diluted into binding buffer (50 mM Tris, 3 mM MgCl$_2$, 1 mg/ml BSA (Sigma A-7888), pH 7.4, which was stored at 4° C. after filtration through a 0.22 m filter, and to which had been freshly added 5 µg/ml aprotinin, 10 µM bestatin, 10 µM diprotin A, no DTT). Aliquots of 100 µl were added to iced 12×75 mm polypropylene tubes containing 100 µl of the appropriate radioligand and 100 µl of test compound at various concentrations. Total (TB) and nonspecific (NS) binding were determined in the absence and presence of 10 µM naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 mM MgCl$_2$) through GF/B filters (Whatman) presoaked for at least 2 h in 0.1% polyethyleneimine. The radioactivity (dpm) retained on the filters was measured with a beta counter after soaking the filters for at least 12 h in minivials containing 6–7 ml scintillation fluid. If the assay is set up in 96-place deep well plates, the filtration is over 96-place PEI-soaked unifilters, which were washed with 3×1 ml wash buffer, and dried in an oven at 55° C. for 2 h. The filter plates were counted in a TopCount (Packard) after adding 50 µl MS-20 scintillation fluid/well.

Functional Assays

The agonist activity of the compounds is measured by determining the degree to which the compounds receptor complex activates the binding of GTP to G-proteins to which the receptors are coupled. In the GTP binding assay, GTP [γ]$^{35}$S is combined with test compounds and membranes from HEK-293S cells expressing the cloned human opioid receptors or from homogenised rat and mouse brain. Agonists stimulate GTP[γ]$^{35}$S binding in these membranes. The EC$_{50}$ and E$_{max}$ values of compounds are determined from dose-response curves. Right shifts of the dose response curve by the delta antagonist naltrindole are performed to verify that agonist activity is mediated through delta receptors.

Procedure for Rat Brain GTP

Rat brain membranes are thawed at 37° C., passed 3 times through a 25-gauge blunt-end needle and diluted in the GTPγS binding (50 mM Hepes, 20 mM NaOH, 100 mM NaCl, 1 mM EDTA, 5 mM MgCl$_2$, pH 7.4, Add fresh: 1 mM DTT, 0.1% BSA). 120 µM GDP final is added membranes dilutions. The EC50 and Emax of compounds are evaluated from 10-point dose-response curves done in 300 µl with the appropriate amount of membrane protein (20 µg/well) and 100000–130000 dpm of GTPγ$^{35}$S per well (0.11–0.14 nM). The basal and maximal stimulated binding are determined in absence and presence of 3 µM SNC-80

Data Analysis

The specific binding (SB) was calculated as TB-NS, and the SB in the presence of various test compounds was expressed as percentage of control SB. Values of IC$_{50}$ and Hill coefficient (n$_H$) for ligands in displacing specifically bound radioligand were calculated from logit plots or curve fitting programs such as Ligand, GraphPad Prism, Sigma-Plot, or ReceptorFit. Values of K$_i$ were calculated from the Cheng-Prussoff equation. Mean±S.E.M. values of IC$_{50}$, K$_i$ and n$_H$ were reported for ligands tested in at least three displacement curves. Biological activity of the compounds of the present invention is indicated in Table 2.

TABLE 2

Biological data.

| Ex. # | HDELTA (nM) | | | RAT BRAIN (nM) | | MOUSE BRAIN (nM) | |
|---|---|---|---|---|---|---|---|
| | IC$_{50}$ | EC$_{50}$ | % EMax | EC$_{50}$ | % EMax | EC$_{50}$ | % EMax |
| 1–15 | 0.247–5.405 | 0.115–338.89 | 84.69–110.25 | 0.563–73.672 | 100.1–176.86 | 0.807–48.164 | 93.36–163.19 |

Receptor Saturation Experiments

Radioligand K$_δ$ values were determined by performing the binding assays on cell membranes with the appropriate radioligands at concentrations ranging from 0.2 to 5 times the estimated K$_{67}$ (up to 10 times if amounts of radioligand required are feasible). The specific radioligand binding was expressed as pmole/mg membrane protein. Values of K$_δ$ and B$_{max}$ from individual experiments were obtained from non-linear fits of specifically bound (B) vs. nM free (F) radioligand from individual according to a one-site model.

Determination of Mechano-Allodynia Using Von Frey Testing

Testing was performed between 08:00 and 16:00 h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill, USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

Testing Protocol

The animals were tested on postoperative day 1 for the FCA-treated group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \text{ g threshold} = 10^{(Xf+k\delta)}/10{,}000$$

where $Xf$=value of the last von Frey hair used (log units); k=tabular value (from Chaplan et al. (1994)) for the pattern of positive/negative responses; and $\delta$=mean difference between stimuli (log units). Here $\delta$=0.224.

Von Frey thresholds were converted to percent of maximum possible effect (% MPE), according to Chaplan et al. 1994. The following equation was used to compute % MPE:

$$\% \text{ MPE} = \frac{\text{Drug treated threshold (g)} - \text{allodynia threshold (g)}}{\text{Control threshold (g)} - \text{allodynia threshold (g)}} \times 100$$

Administration of Test Substance

Rats were injected (subcutaneously, intraperitoneally, intravenously or orally) with a test substance prior to von Frey testing, the time between administration of test compound and the von Frey test varied depending upon the nature of the test compound.

Writhing Test

Acetic acid will bring abdominal contractions when administered intraperitoneally in mice. These will then extend their body in a typical pattern. When analgesic drugs are administered, this described movement is less frequently observed and the drug selected as a potential good candidate.

A complete and typical Writhing reflex is considered only when the following elements are present: the animal is not in movement; the lower back is slightly depressed; the plantar aspect of both paws is observable. In this assay, compounds of the present invention demonstrate significant inhibition of writhing responses after oral dosing of 1–100 μmol/kg.

(i) Solutions Preparation

Acetic acid (AcOH): 120 μL of Acetic Acid is added to 19.88 ml of distilled water in order to obtain a final volume of 20 ml with a final concentration of 0.6% AcOH. The solution is then mixed (vortex) and ready for injection.

Compound (drug): Each compound is prepared and dissolved in the most suitable vehicle according to standard procedures.

(ii) Solutions Administration

The compound (drug) is administered orally, intraperitoneally (i.p.), subcutaneously (s.c.) or intravenously (i.v.)) at 10 ml/kg (considering the average mice body weight) 20, 30 or 40 minutes (according to the class of compound and its characteristics) prior to testing. When the compound is delivered centrally: Intraventricularly (i.c.v.) or intrathecally (i.t.) a volume of 5 μL is administered.

The AcOH is administered intraperitoneally (i.p.) in two sites at 10 ml/kg (considering the average mice body weight) immediately prior to testing.

(iii) Testing

The animal (mouse) is observed for a period of 20 minutes and the number of occasions (Writhing reflex) noted and compiled at the end of the experiment. Mice are kept in individual "shoe box" cages with contact bedding. A total of 4 mice are usually observed at the same time: one control and three doses of drug.

For the anxiety and anxiety-like indications, efficacy has been established in the geller-seifter conflict test in the rat.

For the functional gastrointestina disorder indication, efficacy can be established in the assay described by Coutinho S V et al, in American Journal of Physiology-Gastrointestinal & Liver Physiology. 282(2):G307–16, 2002 February, in the rat.

What is claimed is:

1. A compound of the formula I:

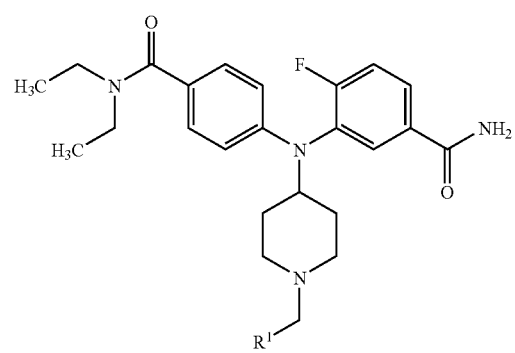

or a salt thereof, wherein:

R¹ is selected from any one of (i) phenyl;

(ii) pyridinyl;

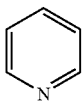

(iii) thienyl;

(iv) furanyl;

(v) imidazolyl;

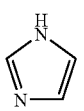

(vi) triazolyl;

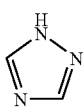

(vii) pyrrolyl

(viii) thiazolyl;

or
(ix) pyridyl-N-oxide

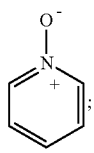

where each said phenyl, pyridinyl, thienyl, furanyl, imidazolyl, triazolyl, pyrrolyl, thiazolyl or pyridyl-N-oxide is optionally substituted by 1, 2 or 3 substituents independently selected from the group of straight and branched $C_1$–$C_6$ alkyl, $NO_2$, $CF_3$, $C_1$–$C_6$ alkoxy, chloro, fluoro, bromo, and iodo.

2. A compound according to claim 1, wherein each said phenyl, pyridinyl, thienyl, furanyl, imidazolyl, triazolyl, pyrrolyl, thiazolyl or pyridyl-N-oxide is optionally substituted by 1, 2 or 3 substituents independently selected from the group of methyl, $CF_3$, chloro, fluoro, bromo, and iodo.

3. A compound according to claim 1, wherein each said phenyl, pyridinyl, thienyl, furanyl, imidazolyl, thiazolyl, pyrrolyl, thiazolyl or pyridyl-N-oxide is optionally substituted by a methyl group.

4. A compound according to claim 1, wherein $R^1$ is pyridinyl, pyrrolyl, thienyl or furanyl.

5. A compound according to claim 1, selected from:
3-[(1-Benzyl-piperidin-4-yl)-(4-diethyl-carbamoyl-phenyl)-amnino]-4-fluoro-benzamide,
3-[(4-Diethylcarbamoyl-phenyl)-(1-pyridin-2-ylmethyl-piperidin-4-yl)-amino]-4-fluoro-benzamide,
3-[(4-Diethylcarbamoyl-phenyl)-(1-thiophen-3-ylmethyl-piperidin-4-yl)-amino]-4-fluoro-benzamide,
3-[(4-Diethylcarbamoyl-phenyl)-(1-furan-3-ylmethyl-piperidin-4-yl)-amino]-4-fluoro-benzamide,
3-[(4-Diethylcarbamoyl-phenyl)-(1-thiophen-2-ylmethyl-piperidin-4-yl)-amino]-4-fluoro-benzamide,
3-[[1-(2,4-Dichloro-benzyl)-piperidin4yl]-(4-diethylcarbam-oyl-phenyl)-amino]-4-fluoro-benzamide,
3-[(4-Diethylcarbamoyl-phenyl)-(1-thiazol-2-ylmethyl-piperidin-4-yl)-amino]-4-fluoro-benzamide,
3-[[1-(4-Bromo-benzyl)-piperidin-4-yl]-(4diethylcarbamoyl-phenyl)-amino]-4-fluoro-benzamide,
3-[(4-Diethylcarbamoyl-phenyl)-(1-furan-2-ylmethyl-piperidin-4-yl)-amino]-4-fluoro-benzamide,
3-[(4-Diethylcarbamoyl-phenyl)-(1-pyridin-4-ylmethyl-piperidin4-yl)-amino]-4-fluoro-benzamide,
3-[[1-(4Chloro-benzyl)-piperidin-4-yl]-(4-diethylcarbamoyl-phenyl)-amino]-4-fluoro-benzamide,
3-[(4-Diethylcarbamoyl-phenyl)-(1-pyridin-3-ylmethyl-piperidin-4-yl)-amino]-4-fluoro-benzamide,
3-{(4-Diethylcarbamoyl-phenyl)-[1-(3H-imidazol-4-ylmethyl)-piperidin-4-yl]-amino}-4-fluoro-benzamide,
3-{(4-Diethylcarbamoyl-phenyl)-[1-(1H-imidazol-2-ylmethyl)-piperidin4-yl ]-amino}-4-fluoro-benzamide and
3-{(4-Diethylcarbamoyl-phenyl)-[1-(1H-pyrrol-2-ylmethyl)-piperidin-4-yl]-amino}-4-fluoro-benzamide, or a salt thereof.

6. A compound according to any one of claims 1 to 5 wherein the salt is a hydrochloride, dihydrochloride, sulfate, tartrate, ditrifluoroacetate or citrate salt.

7. A process for preparing a compound of formula I:

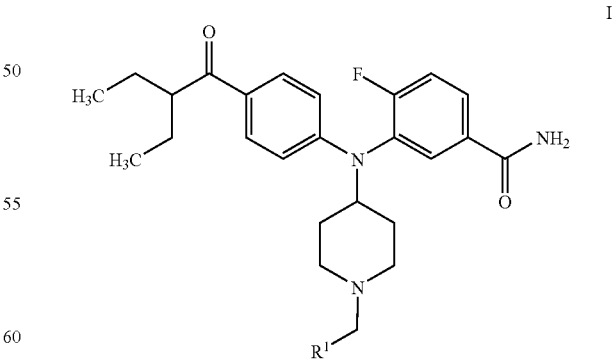

or a slt thereof, wherein:
$R^1$ is selected from the group of phenyl, pyridinyl, thienyl, furanyl, imidazolyl, triazolyl, pyrrolyl, thiazolyl or pyridyl-N-oxide, and wherein each phenyl, pyridinyl, thienyl, furanyl, imidazolyl, triazolyl, pyrrolyl, thiazolyl or pyridyl-N-oxide is optionally substituted by 1,2 or 3 substituents independently selected from the group of straight and branched $C_1$–$C_6$ alkyl, $NO_2$, $CF_3$, $C_1$–$C_6$ alkoxy, chloro, fluoro, bromo, and iodo;
comprising reacting a compound of formula II

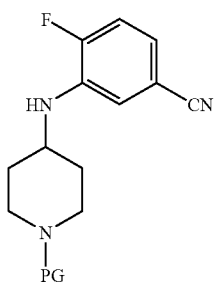

II wherein PG is selected from the group of Boc, CBZ, benzyl and 2,4-dimethoxybenzyl, with N, N-diethyl-4-bromobenzamide, using a palladium catalyst, in the presence of a base, to give a compound of formula III:

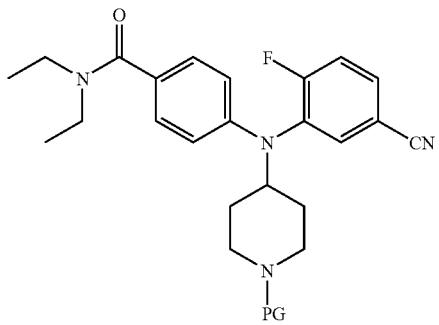

III which is thereafter deprotected, and the deprotected product is alkylated with a compound of the formula of $R^1$—CHO and the alkylated product is hydrolyzed to form the compound of formula I or a salt thereof.

8. A pharmaceutical composition comprising a compound of claim 1 and a pharmaceutically acceptable carrier.

9. A method of treating pain in a subject comprising administering to said subject an effective amount of a compound of claim 1.

10. A compound of formula III

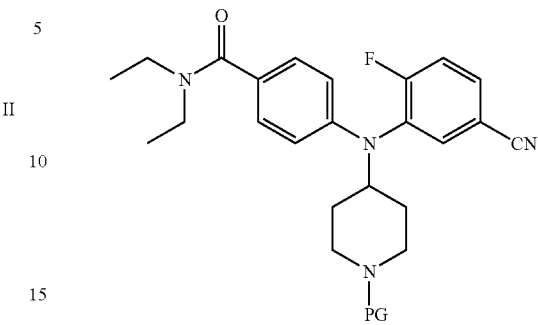

III or a salt thereof, wherein PG is selected from the group of Boc, CBZ, benzyl and 2,4-dimethoxybenzyl.

11. A compound of formula X:

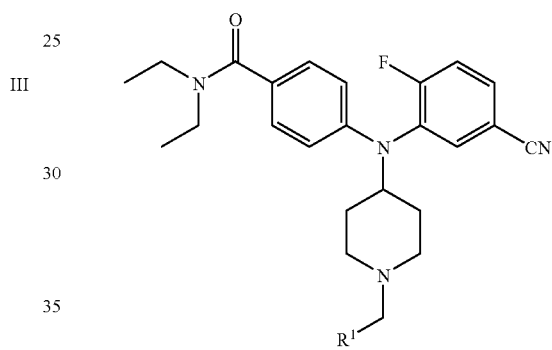

X or a salt thereof, wherein:
  $R^1$ is selected from any one of phenyl, pyridinyl, thienyl, furanyl, imidazolyl, triazolyl, pyrrolyl, thiazolyl, or pyridyl-N-oxide, and wherein each said phenyl, pyridinyl, thienyl, furanyl, imidazolyl, triazolyl, pyrrolyl, thiazolyl or pyridyl-N-oxide is optionally substituted by 1, 2 or 3 substituents independently selected from the group of straight and branched $C_1$–$C_6$ alkyl, $NO_2$, $CF_3$, $C_1$–$C_6$ alkoxy, chloro, fluoro, bromo, and iodo.

* * * * *